United States Patent
Jackson et al.

(10) Patent No.: US 9,527,797 B1
(45) Date of Patent: Dec. 27, 2016

(54) ISOMER-SELECTIVE SYNTHESIS OF METHANOFULLERENES

(71) Applicant: Nano-C, Inc., Westwood, MA (US)

(72) Inventors: Edward A. Jackson, Franklin, MA (US); Henning Richter, Newton, MA (US)

(73) Assignee: NANO-C, INC., Westwood, MA (US)

( * ) Notice: Subject to any disclaimer, the term of this patent is extended or adjusted under 35 U.S.C. 154(b) by 0 days.

(21) Appl. No.: 15/073,335

(22) Filed: Mar. 17, 2016

(51) Int. Cl.
*C07C 67/317* (2006.01)
*C07C 69/618* (2006.01)
*C07C 321/20* (2006.01)

(52) U.S. Cl.
CPC ........... *C07C 67/317* (2013.01); *C07C 69/618* (2013.01); *C07C 321/20* (2013.01); *C07C 2104/00* (2013.01)

(58) Field of Classification Search
CPC ..... C07C 67/317; C07C 69/618; C07C 321/20
See application file for complete search history.

(56) References Cited

U.S. PATENT DOCUMENTS 7,906,797 B2   3/2011  Hummelen et al.
8,481,996 B2   7/2013  Hummelen et al.

FOREIGN PATENT DOCUMENTS

JP   2014-034519 A   2/2014

OTHER PUBLICATIONS

English translation of JP2014-034519, Feb. 24, 2014, pp. 1-86 (orginal publication already on record).*
Bingel, Carsten, "Cyclopropanierung von Fullerenen," Chem. Ber., vol. 126, pp. 1957-1959 (1993).
Cowan, S. R., et al., "Identifying a Threshold Impurity Level for Organic Solar Cells: Enhanced First-Order Recombination Via Well-Defined $PC_{84}BM$ Traps in Organic Bulk Heterojunction Solar Cells and Supporting Information for Identifying a Threshold Impurity Level for Organic Solar Cells: Enhanced First-Order Recombination Via Well-Defined $PC_{84}BM$ Traps in Organic Bulk Heterojunction Solar Cells ," Advanced Functional Materials, vol. 21, pp. 3083-3092, 19 pages (2011).
Dennler, G., et al., "Polymer-Fullerene Bulk-Heterojunction Solar Cells," Advanced Materials, vol. 21, pp. 1-16 (2009).
Etxebarria, I., et al., "Polymer: fullerene solar cells: materials, processing issues, and cell layouts to reach power conversion efficiency over 10%, a review," Journal of Photonics for Energy, vol. 5, pp. 0057214-1-057214-25, 26 pages (2015).
He, F. and Yu, L., "How Far Can Polymer Solar Cells Go? In Need of a Synergistic Approach," The Journal of Physical Chemistry Letters, vol. 2, pp. 3102-3113 (2011).
Hummelen, J. C. et al., "Preparation and Characterization of Fulleroid and Methanofullerene Derivatives," J. Org. Chem., vol. 60, pp. 532-538 (1995).
Ito, T., et al., "Facile Synthesis of [6,6]-Phenyl-$C_{61/71}$-Butyric Acid Methyl Esters via Sulfur Ylides for Bulk-Heterojunction Solar Cell," SYNLETT, vol. 24, pp. 1988-1992 (2013).
Kooistra, F. B. et al., "Increasing the Open Circuit Voltage of Bulk-Heterojunction Solar Cells by Raising the LUMO Level of the Acceptor and Supporting Information for Increasing the Open Circuit Voltage of Bulk-Heterojunction Solar Cells by Raising the LUMO Level of the Acceptor," Organic Letters, vol. 9, No. 4, pp. 551-554, 39 pages (2007).
Lenes, M. et al., "Electron Trapping in Higher Adduct Fullerene-Based Solar Cells and Supporting Information for Electron Trapping in Higher Adduct Fullerene-Based Solar Cells ," Advanced Functional Materials, vol. 19, pp. 3002-3007, 22 pages (2009).
Thilgen, C., et al., "The Covalent Chemistry of Higher Fullerenes: $C_{70}$ and Beyond," Angew. Chem. Int. Ed. Engl., vol. 36, pp. 2269-2280 (1997).
Wang, Y., et al., "Chemoselective Synthesis and Resolution of Chiral [1,9]Methanofullerene[70] Derivatives and Supporting Information for Chemoselective Synthesis and Resolution of Chiral [1,9]Methanofullerene[70] Derivatives," J. Org. Chem., vol. 61, pp. 5198-5199, 22 pages (1996).
Wienk, M. M. et al., "Efficient Methano[70]fullerene/MDMO-PPV Bulk Heterojunction Photovoltaic Cells and Supporting Information for Efficient Methano[70]fullerene/MDMO-PPV Bulk Heterojunction Photovoltaic Cells," Angewandte Chemie, vol. 42, pp. 3371-3375, 7 pages (2003).

\* cited by examiner

*Primary Examiner* — Paul A Zucker
*Assistant Examiner* — Mark Luderer
(74) *Attorney, Agent, or Firm* — Wilmer Cutler Pickering Hale and Dorr LLP

(57) ABSTRACT

[6,6]-Phenyl $C_{71}$ butyric acid derivatives ($C_{70}$-$PCBR_3$) having a selectivity of greater than 95 wt % of the α-isomer are provided by reacting fullerene $C_{70}$ with a dialkyl sulfonium tetrafluoroborate having the formula:

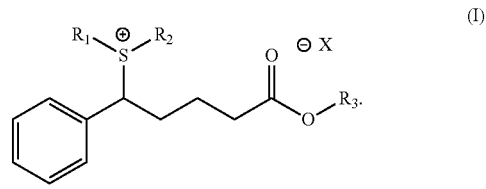

(I)

8 Claims, 2 Drawing Sheets

ISOMER-SELECTIVE SYNTHESIS OF METHANOFULLERENES

FIELD OF THE INVENTION

The invention addresses the synthesis of specific isomers of methano-adducts of C70 and higher fullerenes.

BACKGROUND OF THE INVENTION

Methanofullerenes such as phenyl-$C_{61}$-butyric acid methyl ester ($PC_{60}BM$) and phenyl-$C_{71}$-butyric acid methyl ester ($PC_{70}BM$) are widely used as electron acceptor materials in organic photovoltaic devices (OPV) and organic photodetectors (OPD) (G. Dennler et al., *Adv. Mater.* 2009, 21, 1-16; F. He and L. Yu., *J. Phys. Chem. Lett.* 2011, 2, 3102-3113; I. Etxebarria et al., *Journal of Photonics for Energy* 2015, 5, 057214).

The synthesis of methanofullerenes is most commonly based on [3+2] cycloadditions by the reaction of diazomethanes, diazoacetates, diazoamides or diazoketones (A. Hirsch and M. Brettreich, Fullerenes: Chemistry and Reactions, 2005, Wiley-VCH, ISBN: 3-527-60820-2, pp. 119ff). Also, cyclopropanation reactions by nucleophilic addition of deprotonated α-halo-esters or ketones have been used successfully (C. Bingel, *Chem. Ber.* 1993, 126, 1957-1959). It has been demonstrated that addition of unsymmetrically substituted diazoalkanes leads to two isomers, i.e., [5,6] fulleroids having an open C—C bond on the fullerene cage and [6,6]methanofullerenes (Hummelen et al., *J. Org. Chem.* 1995, 60, 532-538). While fulleroids are formed first, when submitted to heat or irradiation by light they convert quantitative to the latter, resulting in [6,6]methanofullerenes as the thermodynamically stable compound used for OPV and OPD applications (Hummelen et al., *J. Org. Chem.* 1995, 60, 532-538) (Kooistra et al., *Org. Lett.* 2007, 9, 551-554). An additional degree of complexity is reached when $C_{70}$ instead of $C_{60}$ is the reactant. Whereas $C_{60}$ contains only one type of 6-6 bond (a bond between two six membered rings), $C_{70}$ has four, leading to mixtures of regioisomers. Even larger numbers of different regioisomers are formed in the case of multiple (such as bis- and tris-) adducts. A general discussion of isomers among fullerene adducts in the case of fullerene larger than $C_{60}$ (such as $C_{70}$, $C_{76}$, $C_{78}$ and $C_{84}$) can be found in Thilgen et al. (*Angew. Chem. Int. Ed. Engl.* 1997, 36, 2268-2280.). A more specific description of isomers of phenyl-$C_{71}$-butyric acid methyl ester ($PC_{70}BM$) has been provided by Wienk et al. (*Angew. Chem. Int. Ed.* 2003, 42, 3371-3375, U.S. Pat. No. 7,906,797 B2, U.S. Pat. No. 8,481,996 B2). Using a [3+2] cycloaddition of substituted diazomethane (using tosylhydrazone as reactant), products were analyzed using $^1H$ NMR and $^{13}C$ NMR. It was concluded that the major isomer (~85%) is the α-type compound formed by 1,3-dipolar addition to the most "polar" double bond (the C(8)-C(25) bond) yielding a chiral enantiomeric mixture. Two minor isomers (a combined proportion of ~15%) were also identified as achiral stereoisomeric "type" addends, in which the addend is bound to the C(9)-C(10) double bond (the second most "polar" C═C bond in the $C_{70}$ skeleton, after the C(8)-C(25) bond). For simplification, in this document, it will not be differentiated between the enantiomers of the α-isomer, which are referred to collectively as the "α-isomer" or "α-$PC_{70}BM$." Similarly, the two achiral isomers are not addressed individually, and they are collectively referred to as the "β-isomers" or "β-$PC_{70}BM$." The chromatographic separation of these isomers has been found to be extremely challenging and no viable preparative solution exists.

Reactions of semistabilized sulfur ylides generated in situ from corresponding sulfonium salts with $C_{70}$ have been investigated. Such synthetic approach has been initially reported by Ito et al. (*Synlett.* 2013, 24, 1988-1992; JP2014-034519A), who prepared dimethyl (5-methoxy-5-oxo-1-phenylpentyl) sulfonium tetrafluoroborate by bromination of methyl 5-phenylpentanoate at the benzyl position, followed by nucleophilic substitution of the bromide with dimethyl sulfide. After optimization of the reaction with $C_{60}$ resulting in [6,6]-Phenyl-$C_{61}$-butyric acid methyl ester ($PC_{60}BM$) without initial formation of the [5,6] isomer, the reaction was carried out with $C_{70}$, in o-dichlorobenzene (ODCB). [6,6] $PC_{70}BM$ was obtained with 45% isolated yield and the products consisted of the same isomers having a similar component ratio (e.g., α:β 85:15) as in the conventional substituted diazoalkane addition approach by Wienk et al. (*Angew. Chem. Int. Ed.* 2003, 42, 3371-3375, U.S. Pat. No. 7,906,797 B2, U.S. Pat. No. 8,481,996 B2), e.g., 85:15.

While the reaction of $C_{70}$ with dimethyl (5-methoxy-5-oxo-1-phenylpentyl) sulfonium salt resulted in an isomeric mixture, reactions of dimethyl-sulfonium ylides with $C_{70}$ produced methanofullerenes of the type $C_{70}CHCOR$ with regioselectivity (Wang et al., *J. Org. Chem.* 1996, 61, 5198-5199). In yet other instances, using the methyl-, isopropyl-substituted sulfonium ylide of methyl 5-phenylpentanoate resulted in enrichment of α-$PC_{70}BM$ to 95% (based on $^1H$ NMR spectroscopy)(JP2014-034519A).

No systematic correlation of the structure of the substituted sulfonium ylide and the extent of regioselectivity has been established.

SUMMARY

The regioselective synthesis of α-$PC_{70}BR_3$ is achieved by reaction of di-alkyl sulfonium salts (1) with $C_{70}$.

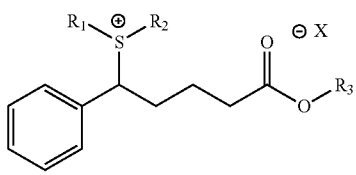

I where $R_1$ and $R_2$ are independently —$CR_4R_5R_6$;
$R_4$, $R_5$, and $R_6$ are independently selected from H, or $C_1$-$C_{12}$ alkyl;
wherein for any one of $R_1$ and $R_2$ no more than one of $R_4$, $R_5$, and $R_6$ can be H;
wherein $R_3$ is independently selected from H and $C_1$-$C_{12}$ alkyl; and
wherein X is an anion selected from $Br^-$, $I^-$, $Cl^-$, $F^-$, $BF_4^-$, $PF_6^-$, $SbF_6^-$, $AsF_6^-$, $OSO_2CH_3^-$, $OSO_2CF_3^-$, $OSO_2C_4F_9^-$, $OSO_2OCH_3^-$, $OCOCH_3^-$, $OCOCF_3^-$, $OSO_2(C_6H_4)CH_3^-$, $OSO_2(C_6H_4)CF_3^-$, $N(SO_2CF_3)_2^-$, $OSO_2CH_2CH_2CH_2CH_2SO_2O^-$—, $OH^-$, $I_3^-$, $N(CN)_2^-$, 7,7-dimethyl-2-oxobicyclo[2.2.1]heptane-1-methanesulfonate, $B(C_6H_5)_4^-$ or $OSO_2OH^-$.

In one or more embodiments, the [6,6]-Phenyl $C_{71}$ butyric acid alkyl derivative is [6,6]-Phenyl $C_{71}$ butyric acid methyl ester.

In one or more embodiments, the reaction provides greater than 95% of the α-isomer.

In one or more embodiments, the reaction provides greater than 98 wt % of the α-isomer.

In one or more embodiments, $R_1$ is iso-propyl, and/or $R_2$ is iso-propyl.

In one or more embodiments, $R_1$ and/or $R_2$ is sec-butyl.

In one or more embodiments, $R_1$ and/or $R_2$ is tert-butyl.

In one or more embodiments, $R_5$ is H.

In one or more embodiments, the method further includes reacting the fullerene $C_{70}$ and the dialkyl sulfonium tetrafluoroborate in the presence of a base.

In one or more embodiments, the base is an organic base.

In one or more embodiments, the base includes 1,8-diazabicyclo[5.4.0]undec-7-ene (DBU).

In one or more embodiments, the regioselective synthesis of α-$PC_{70}BM$ is achieved by reaction of di-alkyl sulfonium salts tetrafluoroborates (Ia) with $C_{70}$.

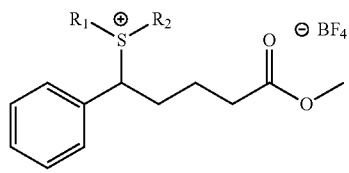

Ia where $R_1$ and $R_2$ are independently —$CR_4R_5R_6$;

$R_4$, $R_5$, and $R_6$ are independently selected from H, or $C_1$-$C_{13}$ alkyl;

wherein for any one of $R_1$ and $R_2$ no more than one of $R_4$, $R_5$, and $R_6$ can be H.

In one or more embodiments, the reaction provides [6,6]-Phenyl $C_{71}$ butyric acid alkyl ester (C70-PCBR$_3$) comprising greater than 95% of the α-isomer.

In one or more embodiments, [6,6]-Phenyl $C_{71}$ butyric acid alkyl ester (C70-PCBR$_3$) is provided having greater than 97% of the α-isomer In one or more embodiments, [6,6]-Phenyl $C_{71}$ butyric acid alkyl ester (C70-PCBR$_3$) is provided having greater than 98% of the α-isomer In one or more embodiments, [6,6]-Phenyl $C_{71}$ butyric acid alkyl ester (C70-PCBR$_3$) is provided having greater than 99% of the α-isomer.

In one or more embodiments, [6,6]-Phenyl $C_{71}$ butyric acid alkyl ester (C70-PCBR$_3$) is provided having greater than 99.5% of the α-isomer.

In one or more embodiments, [6,6]-Phenyl $C_{71}$ butyric acid alkyl ester (C70-PCBR$_3$) is provided having greater than 99.9% of the α-isomer.

In one or more embodiments, [6,6]-Phenyl $C_{71}$ butyric acid alkyl ester (C70-PCBR$_3$) is provided having 97-99.9% of the α-isomer.

In one or more embodiments, [6,6]-Phenyl $C_{71}$ butyric acid alkyl ester (C70-PCBR$_3$) is provided having 98-99.5% of the α-isomer.

In one or more embodiments, [6,6]-Phenyl $C_{71}$ butyric acid alkyl ester (C70-PCBR$_3$) is provided having greater than 97-99% of the α-isomer. The high α-isomer content is achieved by isomer-selective synthesis, without enhancement by separation or removal of the β-isomer.

BRIEF DESCRIPTION OF THE DRAWING

The invention is described with reference to the following figures, which are presented for the purpose of illustration only and are not intended to be limiting of the invention.

DETAILED DESCRIPTION

Figure 1:
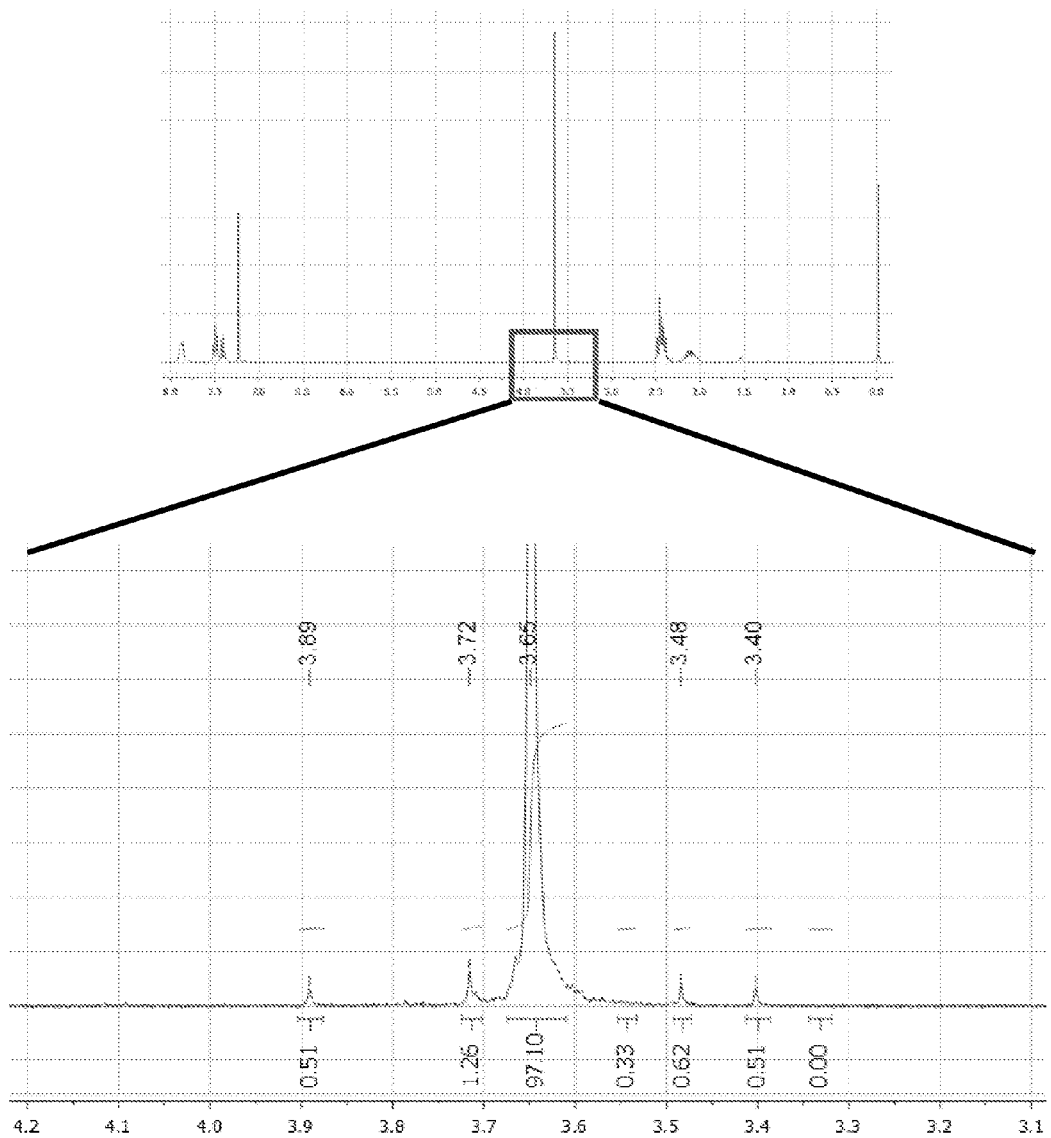
FIG. 1 is an $^1$H NMR of a concentrated sample (30 mg/mL) of α-$PC_{70}BM$ in deuterated chloroform showing the full spectrum (above) and an enlarged view of trace region in the box (below), illustrating the presence of α-$PC_{70}BM$ (3.65 ppm) and the β-$PC_{70}BM$ impurity (3.72 ppm and 3.48 ppm). The abundance of α-$PC_{70}BM$ is measured here to be 98.1% (3.65 ppm+3.89 ppm+3.40 ppm) taking into account the satellites signals for the α-$PC_{70}BM$ methyl singlet (3.89 ppm and 3.40 ppm, indicating the natural occurrence of $^{13}C$).

Di-alkyl-(5-alkoxy-5-oxo-1-phenylpentyl) sulfonium salts I is used for the isomer-selective synthesis of phenyl-$C_{71}$-butyric acid alkyl esters ($PC_{70}BR_3$).

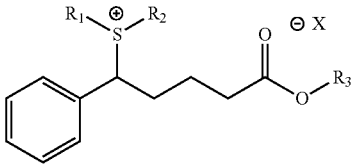

I where $R_1$ and $R_2$ are independently —$CR_4R_5R_6$;

$R_4$, $R_5$, and $R_6$ are independently selected from H, or $C_1$-$C_{12}$ alkyl;

wherein for any one of $R_1$ and $R_2$ no more than one of $R_4$, $R_5$, and $R_6$ can be H;

wherein $R_3$ is independently selected from H and $C_1$-$C_{12}$ alkyl; and wherein X is an anion selected from $Br^-$, $I^-$, $Cl^-$, $F^-$, $BF_4^-$, $PF_6^-$, $SbF_6^-$, $AsF_6^-$, $OSO_2CH_3^-$, $OSO_2CF_3^-$, $OSO_2C_4F_9^-$, $OSO_2OCH_3^-$, $OCOCH_3^-$, $OCOCF_3^-$, $OSO_2(C_6H_4)CH_3^-$, $OSO_2(C_6H_4)CF_3^-$, $N(SO_2CF_3)_2^-$, $OSO_2CH_2CH_2CH_2CH_2SO_2O^-$—, $OH^-$, $I_3^-$, $N(CN)_2^-$, 7,7-dimethyl-2-oxobicyclo[2.2.1]heptane-1-methanesulfonate, $B(C_6H_5)_4^-$ or $OSO_2OH^-$.

As used herein "alkyl" is a linear, cyclic or branched, saturated or unsaturated hydrocarbon.

In one or more embodiments, $R_3$ can be an alkyl ester from $C_1$ to $C_{12}$, while $R_1$ and $R_2$ are independently —$CR_4R_5R_6$ with $R_4$, $R_5$, and $R_6$ being independently selected from H or $C_1$ to $C_{12}$ alkyl. For any one of $R_1$ and $R_2$ no more than one of $R_4$, $R_5$, and $R_6$ can be H. In exemplary embodiments, $R_1$ and $R_2$ can be independently selected from iso-propyl ($R_4$=$R_5$=Me and $R_6$=H), sec-butyl ($R_4$=Me, $R_5$=Et and $R_6$=H), t-butyl ($R_4$=$R_5$=$R_6$=Me), i-pentyl ($R_4$=$R_5$=Me and $R_6$=Et), penta-3-yl ($R_4$=$R_5$=Et and $R_6$=H), hexa-2-yl ($R_4$=Me, $R_5$=Bu and $R_6$=H), hexa-3-yl ($R_4$=Et, $R_5$=Pr and $R_6$=H), 2-methylpenta-2-yl ($R_4$=$R_5$=Me and $R_6$=Pr), 3-methylpenta-3-yl ($R_4$=$R_5$=Et and $R_6$=Me), and 2, 3-dimethylbutan-2-yl ($R_4$=$R_5$=Me and $R_6$=i-Pr), where Me is methyl, Et is ethyl and Pr is propyl. In a particular embodiment, $R_1$ and $R_2$ are both iso-propyl.

In one or more embodiments, $R_3$ includes methyl.

In one or more embodiments, the di-alkyl-(5-alkoxy-5-oxo-1-phenylpentyl) can be compound Ia.

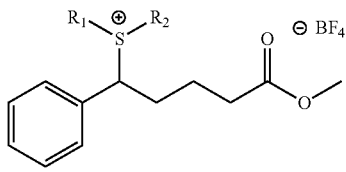

where $R_1$ and $R_2$ are independently —$CR_4R_5R_6$;

$R_4$, $R_5$, and $R_6$ are independently selected from H, or $C_1$-$C_{13}$ alkyl;

wherein for any one of $R_1$ and $R_2$ no more than one of $R_4$, $R_5$, and $R_6$ can be H.

In exemplary embodiments, $R_1$ and $R_2$ can be independently selected from i-propyl ($R_4$=$R_5$=Me and $R_6$=H), sec-butyl ($R_4$=Me, $R_5$=Et and $R_6$=H), t-butyl ($R_4$=$R_5$=$R_6$=Me), i-pentyl ($R_4$=$R_5$=Me and $R_6$=Et), penta-3-yl ($R_4$=$R_5$=Et and $R_6$=H), hexa-2-yl ($R_4$=Me, $R_5$=Bu and $R_6$=H), hexa-3-yl ($R_4$=Et, $R_5$=Pr and $R_6$=H), 2-methylpenta-2-yl ($R_4$=$R_5$=Me and $R_6$=Pr), 3-methylpenta-3-yl ($R_4$=$R_5$=Et and $R_6$=Me), and 2, 3-dimethylbutan-2-yl ($R_4$=$R_5$=Me and $R_6$=i-Pr). In one or more embodiments, the di-alkyl-(5-alkoxy-5-oxo-1-phenylpentyl) can be compound Ia.

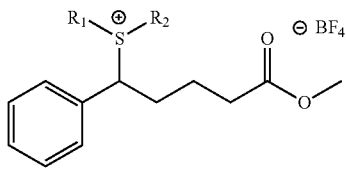

where $R_1$ and $R_2$ are iso-propyl.

A synthetic path targeting selectively α-$PC_{70}BR_3$ (where $R_3$ is as described above) and specifically α-$PC_{70}BM$ (where M is methyl) has been developed. In one or more embodiments, reaction of $C_{70}$ with sulfonium salts of the formula I and Ia provide α-$PC_{70}BR_3$ (where $R_3$ is as described above) and specifically α-$PC_{70}BM$ with a selectivity of greater than 95%, 97% or higher, 98% or higher, 99% or higher, 99.5% or higher and as high as 99.9%. In one or more embodiments, reaction of $C_{70}$ with sulfonium salts of the formula I and Ia provide α-$PC_{70}BR_3$ (where $R_3$ is as described above) and specifically α-$PC_{70}BM$ with a selectivity bounded by any of the values noted above.

Systematic investigation of the reaction of di-alky-(5-methoxy-5-oxo-1-phenylpentyl) sulfonium tetraborates with $C_{70}$ was conducted. The abundance of the different isomers was assessed based on analytical HPLC using a column with Cosmosil Buckyprep material as the stationary phase (from Nacalai Tesque; pyrenylpropyl group bonded silica) and toluene as the mobile phase. For selected experiments, the isomer distribution was also determined by means of peak integration $^1$H NMR of purified final products.

Correlations between the identity of the alkyl-groups $R_1$ and $R_2$ in di-alkyl-(5-methoxy-5-oxo-1-phenylpentyl) sulfonium tetrafluoroborates and the relative abundance of α-$PC_{70}BM$ compared to β-$PC_{70}BM$ were found to be counterintuitive. For example, the α-to-β ratio decreased in changing from iso-propylmethyl- to iso-propylethyl-substitution, while the α-to-β ratio increased in changing from iso-propylethyl- to di-iso-propyl-substitution. While not being bound by any particular mode of operation, it is proposed that the presence of an alkyl substitution at the α-carbon position for both $R_1$ and $R_2$ increases the α-isomer selectivity of the reaction.

Di-alkyl-(5-methoxy-5-oxo-1-phenylpentyl) sulfonium tetrafluoroborates were synthesized beginning with the bromination of methyl 5-phenylpentanoate followed by nucleophilic substitution of the bromide with the corresponding dialkyl sulfide in presence of silver tetrafluoroborate (*Synlett.* 2013, 24, 1988-1992.). The detailed experimental procedures are described below for the different examples.

Two different general schemes (Scheme 1 and Scheme 2), shown below, have been demonstrated for the synthesis of di-alkyl-(5-alkoxy-5-oxo-1-phenylpentyl) sulfonium tetrafluoroborates. In addition, other counter ions such as trifluoromethanesulfonate (triflate, $CF_3SO_3^-$) can be used. Also the use of different leaving groups which may or not become the ion can be envisioned.

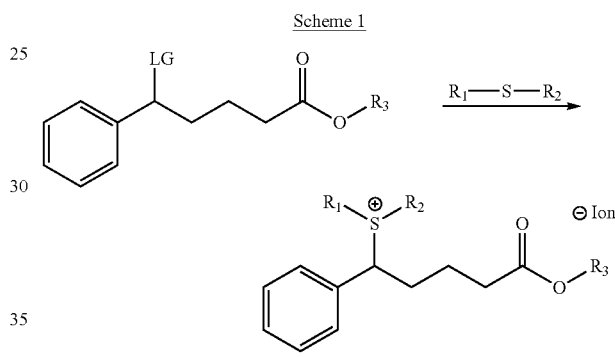

"LG"=Leaving Group. "Ion"=Counter Ion. "LG" may or may not become "Ion". "Ion" may or may not derive from an additional reagent. In Scheme 1, nucleophilic substitution of the leaving group with dialkyl sulfide provides the desired sulfonium salt.

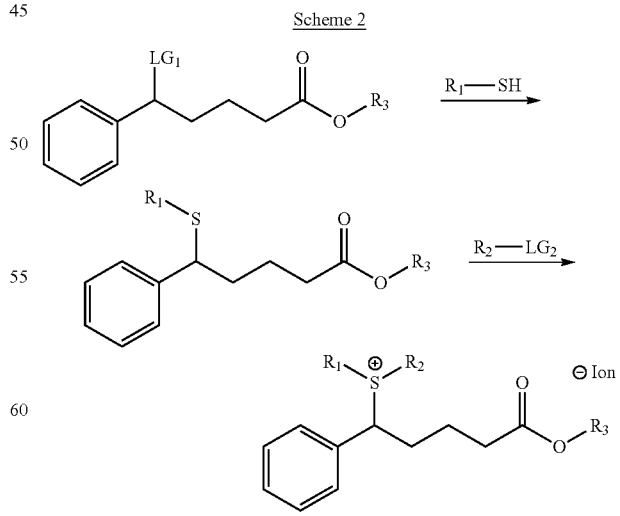

"LG"=Leaving Group. "Ion"=Counter Ion. "$LG_1$" can be the same as "$LG_2$". "$LG_1$" can be the same as "Ion". "$LG_2$"

may or may not become "Ion". "Ion" may or may not derive from an additional reagent. In Scheme 2, nucleophilic substitution of the leaving group with an alkyl thiol to provide a thioether is followed by reaction with an alkylating reagent (and optionally other reagents) to obtain the desired sulfonium salt.

The leaving groups in Scheme 1 (LG) and 2 (LG1 and LG2) can be selected among —Br, —I, —Cl, —F, —$BF_4$, —$PF_6$, —$SbF_6$, —$AsF_6$, —$OSO_2CH_3$, —$OSO_2CF_3$, —$OSO_2C_4F_9$, —$OSO_2OCH_3$, —$OCOCH_3$, —$OCOCF_3$, —$OSO_2(C_6H_4)CH_3$, —$OSO_2(C_6H_4)CF_3$, —$N(SO_2CF_3)_2$, —$OSO_2CH_2CH_2CH_2SO_2O$—, —OH, —$I_3$, —$N(CN)_2$, 7,7-dimethyl-2-oxobicyclo[2.2.1]heptane-1-methanesulfonate, —$B(C_6H_5)_4$ and —$OSO_2OH$. The counter ion ($^-$Ion) may be the same as one of leaving groups, except that it bears a negative charge.

The di-alkyl-(5-methoxy-5-oxo-1-phenylpentyl) sulfonium tetrafluoroborates used as reactants are given in Table 1, together with the yield of their synthesis. Different from the other reactions, methyl, dodecyl functionalization has been carried out in two subsequent steps as described in JP2014-034519A beginning with the substitution of bromine by S—$C_{12}H_{25}$.

TABLE 1

Synthesis of Di-alkyl-(5-methoxy-5-oxo-1-phenylpentyl) sulfonium tetrafluoroborates

| Experiment n° | R1 | R2 | Yield of sulfonium salt synthesis (%) |
|---|---|---|---|
| 1 | $CH_3$ | $C_{12}H_{25}$ | 66 (over two steps) |
| 2 | $CH_3$ | i-$C_3H_7$ | 37 |
| 3 | i-$C_3H_7$ | i-$C_3H_7$ | 34 |
| 4 | $C_2H_5$ | i-$C_3H_7$ | 41 |
| 5 | $C_{12}H_{25}$ | $C_{12}H_{25}$ | 74 |

Subsequent reaction of di-alkyl-(5-alkoxy-5-oxo-1-phenylpentyl) sulfonium salts with $C_{70}$ to provide phenyl-$C_{71}$-butyric acid alkyl esters ($PC_{70}BX$) is shown in Scheme 3.

Scheme 3

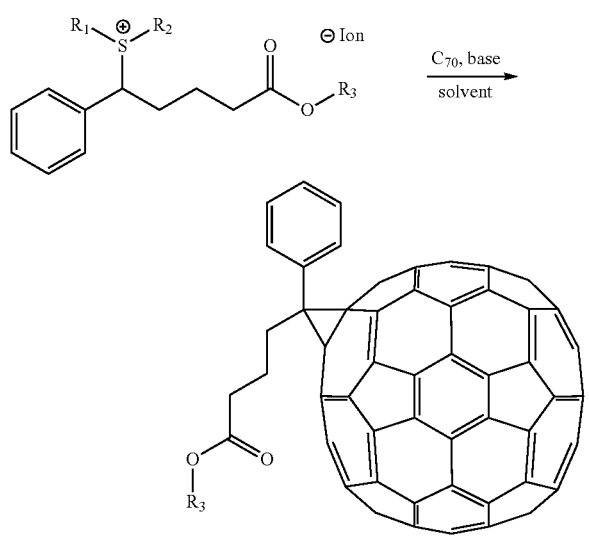

Reaction of di-alkyl-(5-alkoxy-5-oxo-1-phenylpentyl) sulfonium salts with $C_{70}$ to phenyl-$C_{71}$-butyric acid alkyl esters ($PC_{70}BR_3$); "Ion"=Counter Ion.

In one or more embodiments, the reaction is carried out at room temperature (or in slightly elevated temperatures up to ca. 40-50° C.) in presence of base such as DBU (1,8-diazabicyclo[5.4.0]undec-7-ene), DBN (1,5-diazabicyclo[4.3.0]non-5-ene), DABCO (1,4-diazabicyclo(2.2.2)octane), pyridine, 2,6-dimethylpyridine, 2,4,6-trimethylpyridine, DMAP (dimethylaminopyridine), trimethylamine, triethylamine, Hunig's base (N,N-diisopropylethylamine), DMA (dimethylaniline), TMP (2,2,6,6-tetramethylpiperidine), PMP (1,2,2,6,6-pentamethylpiperidine), sodium borohydride, lithium aluminum hydride, sodium hydride, sodium methoxide, lithium methoxide, potassium methoxide, sodium t-butoxide, lithium t-butoxide, potassium t-butoxide, n-butyllithium, t-butyllithium, n-butylmagnesium chloride, t-butylmagnesium chloride, and LiHMDS (lithium hexamethyldisilazide).

In one or more embodiments, the reaction is conducted in an aromatic solvent, such as in o-dichlorobenzene (ODCB).

Figure 2:
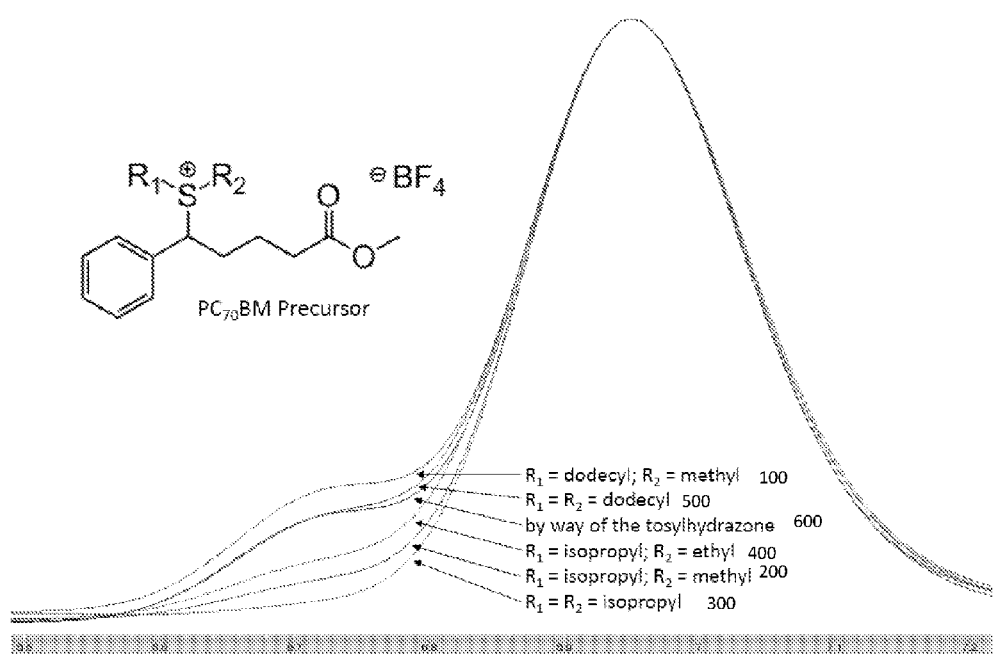
FIG. 2 is an analytical HPLC chromatograph overlay of $PC_{70}BM$ samples made using a range of precursors, in which the leading shoulder is β-$PC_{70}BM$ and the main signal is α-$PC_{70}BM$ (Cosmosil Buckyprep material was used as the stationary phase (from Nacalai Tesque; pyrenylpropyl group bonded silica) and toluene was used as the mobile phase at 1 mL/min.).

HPLC chromatograms of [6,6]-Phenyl $C_{71}$ butyric acid methyl ester produced using the different dialkyl sulfonium salts shown in Table 1 in each of the examples are shown in FIG. 2. In addition, the chromatogram of the product mixture resulting from the currently best established synthesis based on the reaction of tosylhydrazone (a substituted diazoalkane) as described by Hummelen et al. (*J. Org. Chem.* 1995, 60, 532-538.) and Wienk et al. (*Angew. Chem. Int. Ed.* 2003, 42, 3371-3375, U.S. Pat. No. 7,906,797 B2, U.S. Pat. No. 8,481,996 B2) but using irradiation by light for the isomerization of fulleroid to methanofullerene (Kooistra et al., *Org. Lett.* 2007, 9, 551-554) is included as curve 600.

Assessing the results of Examples 1c, 2b, 3b, 4b and 5b below (curves 100, 200, 300, 400 and 500, respectively), it can be established that the identity of the alkyl-groups in the di-alkyl-(5-methoxy-5-oxo-1-phenylpentyl) sulfonium tetrafluoroborates has an effect on the abundance of $\alpha$-$PC_{70}BM$ relative to $\beta$-$PC_{70}BM$. The conventional tosylhydrazone route (curve 600) yielded the expected $\alpha$-to-$\beta$ ratio of ca. 85:15, similar to that obtained using a di-methyl substituted sulfonium salt (Ito et al., *Synlett.* 2013, 24, 1988-1992; JP2014-034519A). Surprisingly, when both methyl groups are replaced by the more bulky dodecyl groups, the ratio of the obtained $\alpha$-$PC_{70}BM$ and $\beta$-$PC_{70}BM$ (curve 500) is substantially unaffected. Based on a steric argument one would expect the dodecyl groups to enhance selectivity to produce more $\alpha$-PC70BM and less $\beta$-PC70BM. It is similarly counterintuitive that the product obtained from the methyldodecyl sulfonium salt (curve 100) actually gives less selectivity (more $\beta$-PC70BM), despite also being more bulky than the dimethyl sulfonium salt precursor. Investigating sulfonium salts substituted with at least one iso-propyl-substitution, it can be seen in FIG. 2 that the relative amount of $\beta$-$PC_{70}BM$ decreases along the trend iso-propylethyl-> to i-propylmethyl> di-iso-propyl, when dialkyl sulfonium salts are used in the preparation of $C_{70}PCBM$. Thus, while the observed change in relative abundance from iso-propylethyl- to iso-propylmethyl sulfonium salts would suggest that decreased steric bulk enhances selectivity, the selectivity surprisingly is improved when di-iso-propyl sulfonium salt (with increased steric bulk) is used in the preparation of $C_{70}PCBR_3$ compounds.

While the assessment of the relative evolution of the $\alpha$-to-$\beta$ ratio by means of HPLC can be considered as being accurate, the determination of absolute values is more difficult, particularly due to incomplete separation of the peaks assigned to $\alpha$- and $\beta$-$PC_{70}BM$. In an effort to determine the upper limit of the $\beta$-$PC_{70}BM$ present, additional analytical HPLC using again a Buckyprep stationary phase but 4:1 cyclohexane:toluene for elution in order to increase the resolution was conducted. Peak integration showed the β-PC$_{70}$BM being at 1.2%. In order to increase even further the level of confidence of our purity assessment, $^1$H NMR using a higher concentration of the analyzed PC$_{70}$BM (30 mg/mL in CDCl$_3$) was conducted. The resulting $^1$NMR spectrum is given in FIG. 1. FIG. 1 shows the $^1$NMR spectrum of a concentrated sample (30 mg/mL) of α-PC$_{70}$BM (3.65 ppm) in deuterated chloroform. The full spectrum is shown first, followed by a larger image of the area shown in the box. Using the procedure described by Wienk et al. (Angew. Chem. Int. Ed. 2003, 42, 3371-3375), i.e., the integration of the three signals representing methoxy groups (3.48 ppm, 3.65 ppm, and 3.72 ppm, as reported by Wienk et al.) shows an area of ≤1.9% for signals representing β-PC$_{70}$BM. However, integration of the baseline at different points (for example ~3.55 ppm and ~3.33 ppm) shows that the noise in proximity to the 3.65 ppm signal for the α-PC$_{70}$BM methyl singlet may be artificially inflating the measured abundance of β-PC$_{70}$BM. We therefore set 1.9% as the upper limit for the abundance of β-PC$_{70}$BM, however, the actual value can be less.

Integration of $^1$H NMR peaks was reported by Wienk et al. (*Angew. Chem. Int. Ed.* 2003, 42, 3371-3375.) to show an abundance of α-PC$_{70}$BM of approximately 85% in the case of the tosylhydrazone approach whereas, using the same $^1$H NMR analysis, reaction of C$_{70}$ with i-propylmethyl-substituted sulfonium salt resulted in 95.0% of α-PC$_{70}$BM. Finally, after reaction of di-iso-propyl-(5-methoxy-5-oxo-1-phenylpentyl) sulfonium tetrafluoroborate with C$_{70}$ using the conditions described in Example 3b, less than or equal to 1.9% β-PC$_{70}$BM could be identified my means of the same analytical approach, that is, greater than 98% α-isomer.

The invention is described with reference to the following examples, which are presented for the purpose of illustration only and are not intended to be limiting of the invention.

EXAMPLE 1A 5-dodecylthio-5-phenylpentanoic acid methyl ester

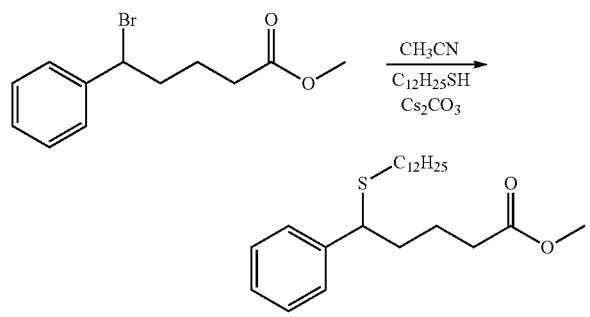

To a clean, dry 250 mL round bottom flask was added a stir bar and 5.41 g (16.6 mmol, 3 eq) of cesium carbonate. The round bottom was sealed and purged three times with inert gas and vacuum. Anhydrous acetonitrile (27.7 mL) was added to the flask via syringe. The solution was cooled to 0° C., allowed to equilibrate for 15 minutes, and 1-dodecanethiol (3.975 mL, 3.36 g, 16.6 mmol, 3 eq) was added cautiously by syringe. Shortly thereafter, a solution of the bromide (1.5 g, 5.53 mmol, 1 eq) in 5.5 mL of anhydrous acetonitrile was added dropwise (over 30 minutes by syringe pump) with the reaction still at 0° C. Once the addition was complete and an additional 15 minutes had passed, the reaction was allowed to warm to room temperature for 5 hours. The reaction was then filtered and 277 mL of ethyl acetate was added to the filtrate. The organic later was washed with brine 3 times in a separatory funnel, dried with magnesium sulfate, filtered, and solvent was removed by rotary evaporation to give crude product. Silica gel chromatography was used with 9:1 hexane:ethyl acetate as eluent to isolate 1.52 g of the product (an oil which then solidified, 70% yield). $^1$H NMR (500 MHz, CDCl$_3$ (set to 7.26 ppm)) δ 7.35-7.15 (m, 5H), 3.74 (t, J=12.5 Hz, 1H), 3.64 (s, 3H), 2.35-1.1 (m, 28H), 0.88 (t, J=11.0 Hz, 3H).

EXAMPLE 1B

Methyldodecyl-(5-methoxy-5-oxo-1-phenylpentyl) sulfonium tetrafluoroborate (2)

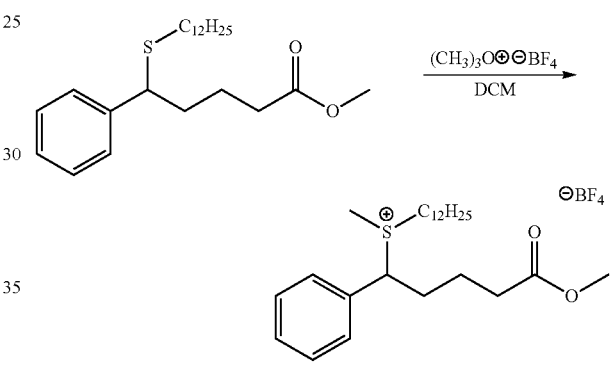

To a clean, dry 50 mL round bottom flask was added a stir bar and 0.886 g (5.99 mmol, 1.5 eq) of trimethyloxonium tetrafluoroborate. The round bottom was sealed and purged three times with inert gas and vacuum. Anhydrous dichloromethane (6 mL) was added and the mixture was cooled to 0° C. To a second round bottom flask was added the thioether starting material. This flask was also sealed and purged three times with inert gas and vacuum. Anhydrous dichloromethane (10 mL) was added to the second flask by syringe, the thioether starting material was dissolved and the solution was taken back up into the same syringe. The solution containing the thioether starting material was then added dropwise by syringe pump to the flask containing the trimethyloxonium tetrafluoroborate over 30 minutes at 0° C. Once the addition was complete, plus an additional 15 minutes, the reaction was allowed to warm to room temperature for 4.5 hours. Dichloromethane was added and the reaction was extracted twice with water. The DCM layer was dried with magnesium sulfate, filtered, and solvent was removed by rotary evaporation to give 1.805 g (94.8% yield) of product. $^1$H NMR (500 MHz, CDCl$_3$ (set to 7.26 ppm)) δ 7.55-7.4 (m, 5H), 4.97 (t, J=13.0 Hz, 1H), 3.64 (s, 1.5H), 3.63 (s, 1.5H), 3.43 (t, J=13.0 Hz, 1H), 3.26-3.14 (m, 0.5H), 3.04 (s, 1.5H), 2.87-2.74 (m, 0.5H), 2.56 (s, 1.5H), 2.43-1.05 (m, 26H), 0.87 (t, J=11.3 Hz, 3H).

EXAMPLE 1C

[6,6]-Phenyl C$_{71}$ butyric acid methyl ester

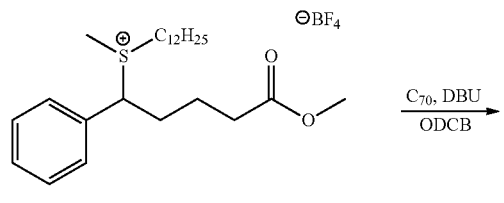

1

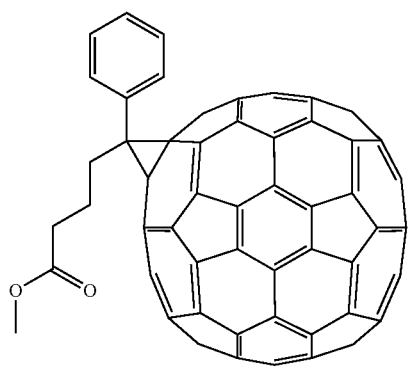

To a clean, dry 250 mL round bottom flask was added a stir bar, 59.3 mg (0.120 mmol, 1 eq) of the sulfonium salt 1, synthesized as described in JP2014-034519A, and 100.8 mg (0.120 mmol, 1 eq) of C$_{70}$. The round bottom was sealed and purged three times with inert gas and vacuum. 84 mL of ODCB (1,2-dichlorobenzene) anhydrous solvent was added by syringe. The reaction was cooled to 0° C. and allowed to equilibrate for 15 minutes. DBU (1,8-diazabicyclo[5.4.0] undec-7-ene, 0.0179 mL, 0.120 mmol, 1 eq) was added over 5 minutes at 0° C. in 4 mL of anhydrous ODCB via syringe. The reaction was allowed to warm slowly with stirring overnight to room temperature. The abundance of α-PC$_{70}$BM was qualitatively determined to be <85% based on analytical HPLC using a column with Cosmosil Buckyprep material as the stationary phase (from Nacalai Tesque; pyrenylpropyl group bonded silica) and toluene as the mobile phase.

EXAMPLE 2A

Methyl-i-propyl-(5-methoxy-5-oxo-1-phenylpentyl) sulfonium tetrafluoroborate (2)

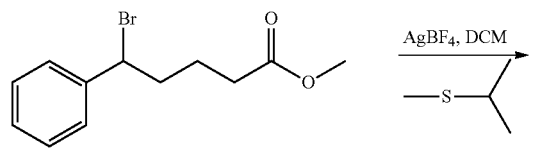

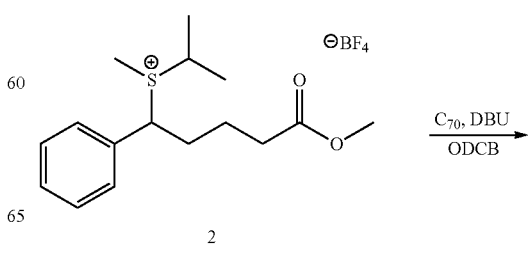

2

To a clean, dry 50 mL round bottom flask was added a stir bar and 1 g (3.69 mmol, 1 eq) of the bromide. The round bottom was sealed and purged three times with inert gas and vacuum. Dichloromethane (4 mL) and methyl isopropyl sulfide (0.998 g, 1.2 mL, 11.1 mmol, 3 eq) were added to the flask sequentially via syringe. The reaction was cooled to 0° C. and allowed to equilibrate for 15 minutes. Silver tetrafluoroborate (718 mg, 3.69 mmol, 1 eq) was added and the reaction was stirred for 4 hours while warming to room temperature slowly. During this time, the reaction was kept in the dark. Dichloromethane was added and the reaction was extracted twice with water. The DCM layer was dried with magnesium sulfate, filtered, and solvent was removed by rotary evaporation. The crude product was taken up in ethyl acetate and loaded onto a small column which was then flushed with copious ethyl acetate to remove impurities. Product was then eluted with acetone. The acetone was removed by rotary evaporation and a small amount of DCM was added to precipitate silica gel that had come through with the acetone. The DCM was filtered to remove silica gel and once again the solution was rotary evaporated to dryness. 500 mg of product was obtained (37% yield). $^1$H NMR (500 MHz, CDCl$_3$ (set to 7.26 ppm)) δ 7.55-7.4 (m, 5H), 4.92 (t, J=13.0 Hz, 0.5H), 4.82 (t, J=13.0 Hz, 0.5H), 3.94 (septet, J=11.3 Hz, 0.5H), 3.63 (s, 1.5H), 3.62 (s, 1.5H), 3.31 (septet, J=11.5 Hz, 0.5H), 3.01 (s, 1.5H), 3.47 (s, 1.5H), 2.45-2.1 (m, 4H), 1.75-1.4 (m, 2H), 1.65 (d, J=11.5 Hz, 1.5H), 1.57 (d, J=11.5 Hz, 1.5H), 1.40 (d, J=11.5 Hz, 1.5H), 1.28 (d, J=11.5 Hz, 1.5H).

EXAMPLE 2B

[6,6]-Phenyl C$_{71}$ butyric acid methyl ester

2

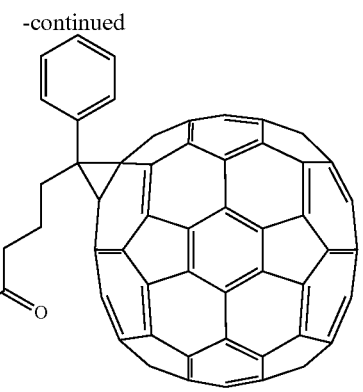

To a clean, dry 250 mL round bottom flask was added a stir bar, 44.2 mg (0.120 mmol, 1 eq) of the sulfonium salt (2), synthesized as described in JP2014-034519A, and 100.8 mg (0.120 mmol, 1 eq) of $C_{70}$. The round bottom was sealed and purged three times with inert gas and vacuum. 84 mL of ODCB (1,2-dichlorobenzene) anhydrous solvent was added by syringe. The reaction was cooled to 0° C. and allowed to equilibrate for 15 minutes. DBU (1,8-diazabicyclo[5.4.0]undec-7-ene, 0.0179 mL, 0.120 mmol, 1 eq) was added over 5 minutes at 0° C. in 4 mL of anhydrous ODCB via syringe. The reaction was allowed to warm slowly with stirring overnight to room temperature. The reaction mixture was rotary evaporated to a small volume of ODCB and subjected to chromatography (silica gel, ODCB to elute $C_{70}$, followed by toluene to collect $PC_{70}BM$). The $PC_{70}BM$ solution was concentrated to a small volume. $PC_{70}BM$ was then precipitated in methanol and isolated by filtration to obtain 60 mg of material (48% crude yield). The abundance of α-$PC_{70}BM$ (desired product, depicted) was determined to be 95.0% based on NMR analysis. $^1$H NMR (500 MHz, CDCl$_3$ (set to 7.26 ppm)) δ 7.95-7.40 (m, 5H), 3.75 (β, s, 0.08H), 3.68 (α, s, 2.85H), 3.51 (β, s, 0.07H), 2.53-2.40 (m, 4H), 2.27-2.02 (m, 6H). This abundance was qualitatively corroborated by analytical HPLC using a column with Cosmosil Buckyprep material as the stationary phase (from Nacalai Tesque; pyrenylpropyl group bonded silica) and toluene as the mobile phase.

EXAMPLE 3A di-i-propyl-(5-methoxy-5-oxo-1-phenylpentyl) sulfonium tetrafluoroborate (3)

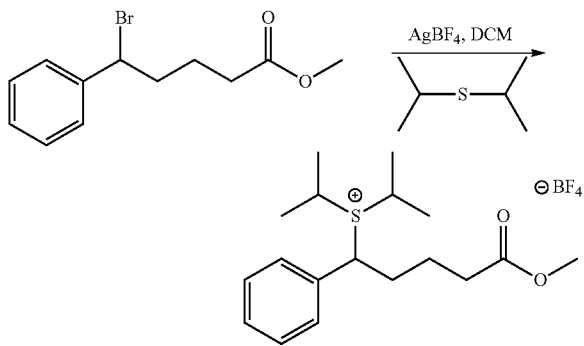

To a clean, dry 50 mL round bottom flask was added a stir bar and 1 g (3.69 mmol, 1 eq) of the bromide. The round bottom was sealed and purged three times with inert gas and vacuum. Dichloromethane (4 mL) and diisopropyl sulfide (1.31 g, 1.61 mL, 11.1 mmol, 3 eq) were added to the flask sequentially via syringe. The reaction was cooled to 0° C. and allowed to equilibrate for 15 minutes. Silver tetrafluoroborate (718 mg, 3.69 mmol, 1 eq) was added and the reaction was stirred for 4 hours while warming to room temperature slowly. During this time, the reaction was kept in the dark. Dichloromethane was added and the reaction was extracted twice with water. The DCM layer was dried with magnesium sulfate, filtered, and solvent was removed by rotary evaporation. The crude product was taken up in ethyl acetate and loaded onto a small column which was then flushed with copious ethyl acetate to remove impurities. Product was then eluted with acetone. The acetone was removed by rotary evaporation and a small amount of DCM was added to precipitate silica gel that had come through with the acetone. The DCM was filtered to remove silica gel and once again the solution was rotary evaporated to dryness. 500 mg of product was obtained (34% yield). $^1$H NMR (500 MHz, CDCl$_3$ (set to 7.26 ppm)) δ 7.6-7.3 (m, 5H), 5.37 (dd, J=5.5 Hz, J=17.0 Hz, 0.1H), 4.94 (t, J=12.8 Hz, 0.9H), 4.12 (septet, J=11.5 Hz, 0.9H), 3.64 (s, 3H), 3.14 (septet, J=11.5 Hz, 0.9H), 2.99 (septet, J=11.1 Hz, 0.2H), 2.8-1.0 (m, 6H), 1.76 (d, J=11.5 Hz, 3H), 1.70 (d, J=11.5 Hz, 3H), 1.43 (d, J=11.5 Hz, 3H), 1.24 (d, J=11.5 Hz, 3H).

EXAMPLE 3B

[6,6]-Phenyl $C_{71}$ butyric acid methyl ester

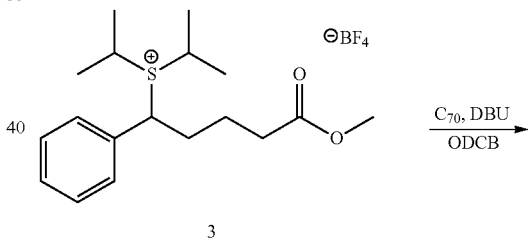

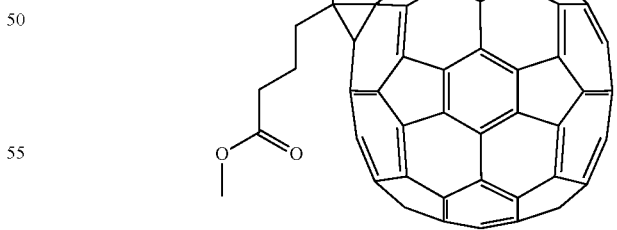

To a clean, dry 500 mL round bottom flask was added a stir bar and 955 mg (1.136 mmol, 1 eq) of $C_{70}$. The round bottom was sealed and purged three times with inert gas and vacuum. 220 mL of ODCB (1,2-dichlorobenzene) anhydrous solvent was added by cannula. Sulfonium salt (3) (450 mg, 1.136 mmol, 1 eq) was taken into 20 mL of anhydrous ODCB and added to the reaction by syringe. The reaction was cooled to 0° C. and allowed to equilibrate for 30 minutes. DBU (1,8-diazabicyclo[5.4.0]undec-7-ene, 0.170 mL, 1.136 mmol, 1 eq) was added dropwise over 10 minutes at 0° C. in 20 mL of anhydrous ODCB via syringe. The reaction was allowed to warm slowly to room temperature and stir over 3 days. The reaction mixture was rotary evaporated to a small volume of ODCB and subjected to chromatography (silica gel, ODCB used to elute $C_{70}$, followed by increasing ratio of toluene to ODCB to collect $PC_{70}BM$). The $PC_{70}BM$ solution was concentrated to dryness and dissolved in a small volume of toluene. The $PC_{70}BM$ solution was then subjected to high pressure sodium lamp irradiation in order to convert minor amounts of [5,6] adduct to [6,6] adduct. A small amount of $PC_{60}BM$ impurity was then removed by preparative intermediate pressure liquid chromatography using a column with Cosmosil PBB material as the stationary phase (from Nacalai Tesque; pentabromobenzyl group bonded silica) and toluene as the mobile phase. The collected material was then further purified by preparative intermediate pressure liquid chromatography using a column with Cosmosil Buckyprep material as the stationary phase (from Nacalai Tesque; pyrenylpropyl group bonded silica) and toluene as the mobile phase. Fractions containing pure product were combined. The solution was concentrated to a small volume. $PC_{70}BM$ was then precipitated in methanol and isolated by filtration to obtain 250 mg of material (21% yield). The sample was left in an oven overnight at 70° C. under reduced pressure to remove residual solvent. α-$PC_{70}BM$ (desired product, depicted) was obtained exclusively, based on NMR analysis. $^1H$ NMR (500 MHz, $CDCl_3$ (set to 7.26 ppm)) δ 7.95-7.40 (m, 5H), 3.68 (α, s, 3.00H), 2.53-2.40 (m, 4H), 2.27-2.02 (m, 6H). β-$PC_{70}BM$ was not detected by regular $^1H$ NMR, nor was it detected by analytical HPLC using a column with Cosmosil Buckyprep material as the stationary phase (from Nacalai Tesque; pyrenylpropyl group bonded silica) and toluene as the mobile phase.

EXAMPLE 4A ethyl-i-propyl-(5-methoxy-5-oxo-1-phenylpentyl) sulfonium tetrafluoroborate (4)

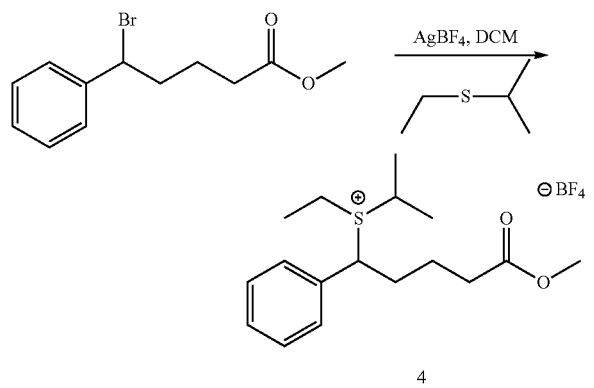

4

To a clean, dry 50 mL round bottom flask was added a stir bar and 0.5 g (1.84 mmol, 1 eq) of the bromide. The round bottom was sealed and purged three times with inert gas and vacuum. Dichloromethane (2 mL) and isopropyl ethyl sulfide (576.5 mg, 0.698 mL, 5.53 mmol, 3 eq) were added to the flask via syringe. The reaction was cooled to 0° C. and allowed to equilibrate for 40 minutes. Silver tetrafluoroborate (359 mg, 1.84 mmol, 1 eq) was added and the reaction was stirred overnight while warming to room temperature slowly. During this time, the reaction was kept in the dark. Dichloromethane was added and the reaction was extracted twice with water. The DCM layer was dried with magnesium sulfate, filtered, and solvent was removed by rotary evaporation. The crude product was taken up in ethyl acetate, and left in the freezer overnight. It was then loaded onto a small column which was flushed with copious ethyl acetate to remove impurities. Product was then eluted with acetone. The acetone was removed by rotary evaporation and a small amount of DCM was added to precipitate silica gel that had come through with the acetone. The DCM was filtered to remove silica gel and once again the solution was rotary evaporated to dryness. 286 mg of product (6) was obtained (41% yield). $^1H$ NMR (500 MHz, $CDCl_3$ (set to 7.26 ppm)) δ 7.6-7.4 (m, 5H), 4.99 (t, J=12.9 Hz, 0.5H), 4.86 (t, J=12.9 Hz, 0.5H), 4.08 (septet, J=11.5 Hz, 0.65H), 3.7-3.4 (m, 3.65H), 3.31 (quintet, J=11.3 Hz, 0.5H), 3.18 (sextet, J=12.0 Hz, 0.6H), 2.98 (sextet, J=12.0 Hz, 0.6H), 2.5-2.1 (m, 4.5H), 1.8-1.2 (m, 9H), 1.01 (t, J=12.5 Hz, 1.5H).

EXAMPLE 4B

[6,6]-Phenyl $C_{71}$ butyric acid methyl ester

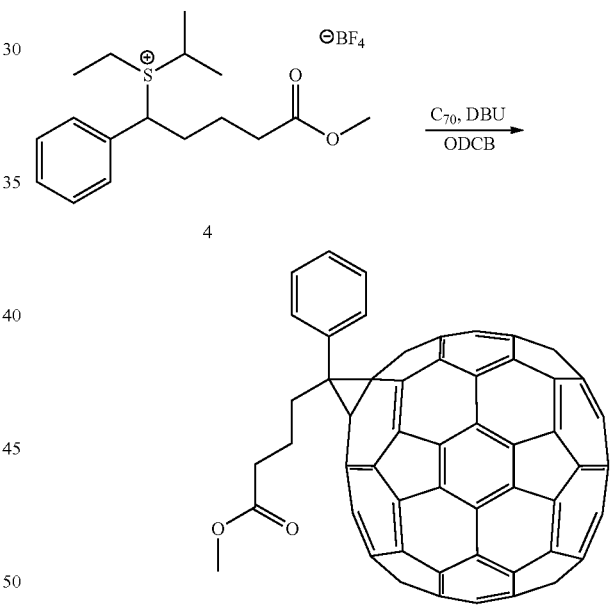

To a clean, dry 50 mL round bottom flask was added a stir bar, 45.5 mg (0.119 mmol, 1 eq) of the sulfonium salt (6) and 100 mg (0.119 mmol, 1 eq) of $C_{70}$. The round bottom was sealed and purged three times with inert gas and vacuum. 9 mL of ODCB (1,2-dichlorobenzene) anhydrous solvent was added by syringe. The reaction was cooled to 0° C. and allowed to equilibrate for 15 minutes. DBU (1,8-diazabicyclo[5.4.0]undec-7-ene, 0.0178 mL, 0.119 mmol, 1 eq) was added over 5 minutes at 0° C. in 1 mL of anhydrous ODCB via syringe. The reaction was allowed to warm slowly with stirring overnight to room temperature. This abundance of α-$PC_{70}BM$ (desired product, depicted) was qualitatively greater than that obtained from the didodecyl precursor but surprisingly less than that obtained from the methyl isopropyl precursor. α-Isomer abundance was determined by analytical HPLC using a column with Cosmosil Buckyprep material as the stationary phase (from Nacalai Tesque; pyrenylpropyl group bonded silica) and toluene as the mobile phase.

EXAMPLE 5A didodecyl-(5-methoxy-5-oxo-1-phenylpentyl) sulfonium tetrafluoroborate (5)

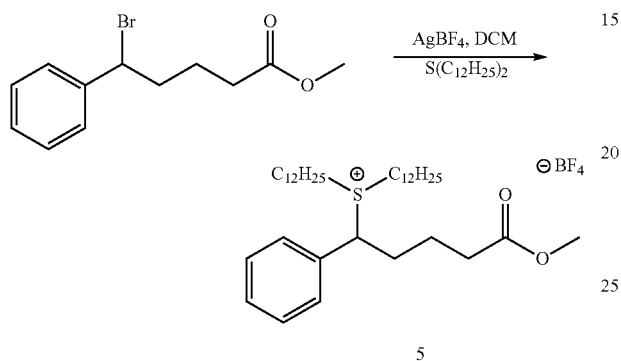

To a clean, dry 50 mL round bottom flask was added a stir bar and 0.5 g (1.84 mmol, 1 eq) of the bromide. The round bottom was sealed and purged three times with inert gas and vacuum. Solid isopropyl ethyl sulfide (2.05 g, 5.53 mmol, 3 eq) dissolved in dichloromethane (2 mL) was added to the flask via syringe. The reaction was cooled to 0° C. and allowed to equilibrate for 40 minutes. The reaction mixture was observed to freeze. Silver tetrafluoroborate (359 mg, 1.84 mmol, 1 eq) was added and the reaction was stirred overnight while warming to room temperature. During this time, the reaction was kept in the dark. Dichloromethane was added and the reaction was extracted twice with water. The DCM layer was dried with magnesium sulfate, filtered, and solvent was removed by rotary evaporation. The crude product was taken up in ethyl acetate, and left in the freezer overnight. Silica TLC was used to adjust the conditions used for further isolation versus other sulfonium salt examples. Ethyl Acetate was removed by evaporation and the product mixture was redissolved in a 7:3 ratio of cyclohexane and ethyl acetate. This solution was loaded onto a small column which was flushed with copious amounts of a 7:3 ratio of cyclohexane:ethyl acetate to remove impurities. Product was then eluted with ethyl acetate. The ethyl acetate was removed by rotary evaporation to give 884 mg of the desired product (7) (74% yield). $^1$H NMR (500 MHz, CDCl$_3$ (set to 7.26 ppm)) δ 7.6-7.4 (m, 5H), 5.07 (t, J=13.0 Hz, $^1$H), 3.63 (s, 3H), 3.52 (octet, J=12.5 Hz, 2H), 3.20 (quintet, J=9.3 Hz, 1H), 2.92 (quintet, J=9.3, Hz, 1H), 2.4-1.0 (m, 46H), 0.88 (t, J=11.5 Hz, 6H).

EXAMPLE 5B

[6,6]-Phenyl C$_{71}$ butyric acid methyl ester

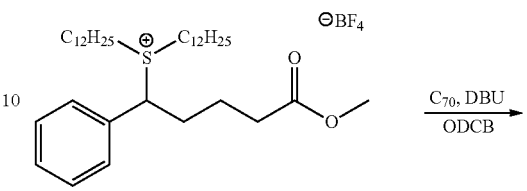

To a clean, dry 50 mL round bottom flask was added a stir bar, 77.2 mg (0.119 mmol, 1 eq) of the sulfonium salt (7) and 100 mg (0.119 mmol, 1 eq) of C$_{70}$. The round bottom was sealed and purged three times with inert gas and vacuum. 9 mL of ODCB (1,2-dichlorobenzene) anhydrous solvent was added by syringe. The reaction was cooled to 0° C. and allowed to equilibrate for 15 minutes. DBU (1,8-diazabicyclo[5.4.0]undec-7-ene, 0.0178 mL, 0.119 mmol, 1 eq) was added over 5 minutes at 0° C. in 1 mL of anhydrous ODCB via syringe. The reaction was allowed to warm slowly with stirring overnight to room temperature. This abundance of α-PC$_{70}$BM (desired product, depicted) was qualitatively similar to the product mixture that is obtained from the more traditional tosylhydrazone precursor (~85%). α-Isomer abundance was determined by analytical HPLC using a column with Cosmosil Buckyprep material as the stationary phase (from Nacalai Tesque; pyrenylpropyl group bonded silica) and toluene as the mobile phase.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. A method of making [6,6]-Phenyl $C_{71}$ butyric acid methyl ester comprising:
reacting fullerene $C_{70}$ with a dialkyl sulfonium salt having the formula:

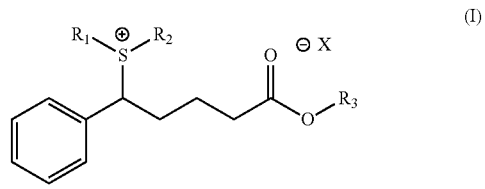

where $R_1$ and $R_2$ are iso-propyl; $R_3$ is methyl; and X an anion selected from $Br^-$, $I^-$, $Cl^-$, $F^-$, $BF_4^-$, $PF_6^-$, $SbF_6^-$, $AsF_6^-$, $OSO_2CH_3^-$, $OSO_2CF_3^-$, $OSO_2C_4F_9^-$, $OSO_2OCH_3^-$, $OCOCH_3^-$, $OCOCF_3^-$, $OSO_2(C_6H_4)CH_3^-$, $OSO_2(C_6H_4)CF_3^-$, $N(SO_2CF_3)_2^-$, $OSO_2CH_2CH_2CH_2CH_2SO_2O^-$—, $OH^-$, $I_3^-$, $N(CN)_2^-$, 7,7-dimethyl-2-oxobicyclo[2.2.1]heptane-1-methane-sulfonate, $B(C_6H_5)_4^-$ or $OSO_2OH^-$,
to provide [6,6]-Phenyl $C_{71}$ butyric acid methyl ester ($C_{70}$-PCBM) comprising greater than 97 wt % of the α-isomer.

2. The method of claim 1, wherein the reaction provides greater than 98 wt % selectivity of the α-isomer.

3. The method of claim 1, further comprising reacting the fullerene $C_{70}$ and the dialkyl sulfonium tetrafluoroborate in the presence of a base.

4. The method of claim 3, wherein the base comprises an organic base.

5. The method of claim 4, wherein the base comprises 1,8-diazabicyclo[5.4.0]undec-7-ene (DBU).

6. The method of claim 1, wherein the dialkyl sulfonium salt has the formula:

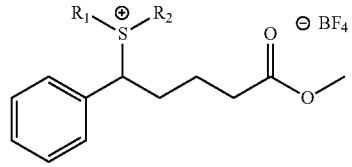

where $R_1=R_2=$iso-propyl.

7. [6,6]-Phenyl $C_{71}$ butyric acid methyl ester ($C_{70}$-PCBM) comprising greater than 98% of the α-isomer.

8. [6,6]-Phenyl $C_{71}$ butyric acid methyl ester ($C_{70}$-PCBM) comprising greater than 99% of the α-isomer.

* * * * *